United States Patent [19]

Rauleder et al.

[11] Patent Number: 5,456,801
[45] Date of Patent: Oct. 10, 1995

[54] STORAGE-STABLE SOLUTIONS OF CARBONATED MAGNESIUM ETHYLATE IN ETHANOL AND THEIR PREPARATION AND USE

[75] Inventors: Hartwig Rauleder; Burkhard Standke; Hans-Joachim Kötzsch; Reinhold Schork, all of Rheinfelden, Germany

[73] Assignee: Huels Aktiengesellschaft, Marl, Germany

[21] Appl. No.: 141,616

[22] Filed: Oct. 27, 1993

[30] Foreign Application Priority Data

Nov. 7, 1992 [DE] Germany ............. 42 37 701.3

[51] Int. Cl.$^6$ ............. D21H 17/12; D21H 17/74
[52] U.S. Cl. ............. 162/160; 162/158; 162/181.2; 252/380; 252/383; 502/172; 502/173
[58] Field of Search ............. 162/160, 158, 162/181.2; 252/380, 381, 382, 383, 384, 385, 397, 398, 399, 42.7, 25, 18; 106/284.03, 413; 502/127, 111, 172, 173; 422/1, 32

[56] References Cited

U.S. PATENT DOCUMENTS

| | | | |
|---|---|---|---|
| 2,895,913 | 7/1959 | Carlyle et al. | 252/18 |
| 3,150,089 | 9/1964 | Hunt | 252/33 |
| 3,277,002 | 10/1966 | Hunt et al. | |
| 3,676,182 | 7/1972 | Smith | 427/316 |
| 3,816,310 | 6/1974 | Hunt | 252/32.7 |
| 4,540,679 | 9/1985 | Arzoumanidis et al. | 502/111 |
| 4,771,024 | 9/1988 | Nestlerode et al. | 502/127 |
| 5,104,997 | 4/1992 | Kamienski et al. | 556/130 |
| 5,162,277 | 11/1992 | Job | 502/124 |

FOREIGN PATENT DOCUMENTS

| | | | |
|---|---|---|---|
| 1285927 | 7/1991 | Canada | C08F 4/64 |
| 0236082 | 9/1987 | European Pat. Off. | |
| 0491128 | 6/1992 | European Pat. Off. | |

*Primary Examiner*—W. Gary Jones
*Assistant Examiner*—Jose A. Fortuna
*Attorney, Agent, or Firm*—Oblon, Spivak, McClelland, Maier & Neustadt

[57] ABSTRACT

The invention relates to storage-stable solutions of carbonated magnesium ethylate of the formula $Mg(C_2H_5O)_2 \cdot (CO_2)_n$ in ethanol and processes for their preparation, wherein (1) the magnesium content of the solution is 2.5 to 6% by weight, based on the total solution, and the $CO_2$ content (n) is 1.55 to 1.85, (2) the magnesium content of the solution is 1.5 to 2.5% by weight, based on the total solution, and the $CO_2$ content (n) being 1.55 to 1.90 or (3) the magnesium content of the solution is less than 1.5% by weight, based on the total solution, and the $CO_2$ content (n) is 1.55 to 2.2.

2 Claims, No Drawings

STORAGE-STABLE SOLUTIONS OF CARBONATED MAGNESIUM ETHYLATE IN ETHANOL AND THEIR PREPARATION AND USE

BACKGROUND OF THE INVENTION

1. Field of the Invention

The invention relates to storage-stable solutions of carbonated magnesium ethylate of the formula $Mg(C_2H_5O)_2 (CO_2)_n$ in ethanol.

The invention furthermore relates to a process for the preparation of storage-stable solutions of carbonated magnesium ethylate of the formula $Mg(C_2H_5O)_2 (CO_2)_n$ in ethanol either by reacting metallic magnesium with ethanol and $CO_2$ or by reacting magnesium ethylate in ethanol with $CO_2$.

The invention also relates to the use of storage-stable solutions of carbonated magnesium ethylate in ethanol for the preservation of paper and for the preparation of catalysts for the polymerization of olefins.

2. Background of the Invention

Magnesium alcoholates are, as a rule, not very soluble or virtually insoluble in the corresponding alcohols. An exception is magnesium methylate, which has a solubility of up to about 12% by weight in methanol.

A technically simple method for increasing the solubility of magnesium alcoholates is carbonation. Gaseous, liquid or solid $CO_2$ is introduced into a suspension of the magnesium alcoholate in the corresponding alcohol. A soluble $CO_2$ adduct forms. In the case of magnesium ethylate, the $CO_2$ adduct is soluble with a concentration of more than 30% by weight in ethanol, whereas pure magnesium ethylate is virtually insoluble in ethanol.

Alcohol-soluble carbonated magnesium alkoxides are widely used. Thus, for example, magnesium alkoxides brought into solution by carbonation can be used in the long-term preservation of paper, in particular books, and can replace the zinc alkyls which are likewise used for this purpose but present problems during use.

A further field of use is the preparation of catalysts for the polymerization of olefins. For this purpose, spherical magnesium ethylate is prepared, for example, by spray drying or homogeneous precipitation of carbonated magnesium ethylate solutions and, if required, subsequent decarbonation.

It is known in principle that solutions of carbonated magnesium alcoholates can be prepared according to the two reaction schemes below: (1) reaction of metallic magnesium with an alcohol ROH and $CO_2$ (equation 1) and (2) reaction of a magnesium alkoxide with $CO_2$ (equation 2):

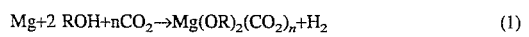

$$Mg + 2\ ROH + nCO_2 \rightarrow Mg(OR)_2(CO_2)_n + H_2 \quad (1)$$

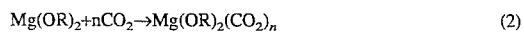

$$Mg(OR)_2 + nCO_2 \rightarrow Mg(OR)_2(CO_2)_n \quad (2)$$

where R denotes an alkyl group and n is an integer such that $0 \leq n \leq 2$.

European Patent 0,236,082 teaches the preparation of carbonated magnesium alkoxides by reacting magnesium alkoxides with $CO_2$ in a solvent. Preferred solvents are alcohols. In particular, the preparation of carbonated magnesium ethylate by reacting magnesium ethylate with $CO_2$ in ethanol as a solvent is disclosed.

In "Reagents for Organic Synthesis" Vol. 1, page 631, Fieser and Fieser describe the preparation of carbonated magnesium methylate by two different routes: (1) reaction of a suspension of magnesium methylate in methanol with $CO_2$ and (2) the reaction of magnesium turnings with methanol to give magnesium methylate. After the methanol has been partially stripped off at 50° C. and reduced pressure, dimethylformamide is added as a solvent and $CO_2$ is passed into this solution. The remaining methanol is distilled off, and a slightly yellow solution of carbonated magnesium methylate in dimethylformamide is obtained.

However, the alcoholic solutions of carbonated magnesium alkoxides according to the prior art are strongly yellow to red. Further, the discoloration can increase with increasing storage times. In addition, precipitation or gel formation can occur on storage for several weeks. The industrial use of such solutions is considerably limited. For example, colored solutions cannot be used for the long-term preservation of books. Further, solutions in which there is a danger of uncontrolled precipitation cannot be used for the preparation of catalysts based on magnesium alkoxide.

SUMMARY OF THE INVENTION

It is the object of the invention to prepare storage-stable solutions of carbonated magnesium ethylate which remain virtually colorless even over a relatively long period and exhibit neither precipitation nor gel formation.

It has now been found, surprisingly, that, as a result of establishing defined magnesium and $CO_2$ concentrations in solutions of carbonated magnesium ethylate, coloration, precipitation and gel formation do not occur even during storage over long periods.

DETAILED DESCRIPTION OF THE PREFERRED EMBODIMENTS

The present invention therefore relates to storage-stable solutions of carbonated magnesium ethylate of the formula $Mg(C_2H_5O)_2 (CO_2)_n$ in ethanol, wherein (1) the magnesium content of the solution is of from 2.5 to 6% by weight, based on the total solution, and the $CO_2$ content (n) is of from 1.55 to 1.85, (2) the magnesium content of the solution is of from 1.5 to 2.5% by weight, based on the total solution, and the $CO_2$ content (n) is of from 1.55 to 1.90 or (3) the magnesium content of the solution is less than 1.5% by weight, based on the total solution, and the $CO_2$ content (n) is of from 1.55 to 2.2.

The present invention furthermore relates to a process for the preparation of storage-stable solutions of carbonated magnesium ethylate of the formula $Mg(C_2H_5O)_2 (CO_2)_n$ in ethanol by reacting metallic magnesium with ethanol and $CO_2$, wherein (1) the magnesium content of the solution is adjusted to values of from 2.5 to 6% by weight, based on the total solution, and the $CO_2$ content is adjusted to values (n) of from 1.55 to 1.85, (2) the magnesium content of the solution is adjusted to values of from 1.5 to 2.5% by weight, based on the total solution, and the $CO_2$ content is adjusted to values (n) of from 1.55 to 1.90 or (3) the magnesium content of the solution is adjusted to values of less than 1.5% by weight, based on the total solution, and the $CO_2$ content is adjusted to values (n) of from 1.55 to 2.2.

The invention further relates to a process for the preparation of storage-stable solutions of carbonated magnesium ethylate of the formula $Mg(C_2H_5O)_2 (CO_2)_n$ in ethanol by reacting magnesium ethylate in ethanol with $CO_2$, wherein (1) the magnesium content of the solution is adjusted to values of from 2.5 to 6% by weight, based on the total solution, and the $CO_2$ content is adjusted to values (n) of from 1.55 to 1.85, (2) the magnesium content of the solution is adjusted to values of from 1.5 to 2.5% by weight, based on the total solution, and the $CO_2$ content is adjusted to values (n) of from 1.55 to 1.90 or (3) the magnesium content of the solution is adjusted to values of less than 1.5% by weight, based on the total solution, and the $CO_2$ content is adjusted to values (n) of from 1.55 to 2.2.

The present invention also relates to the use of these storage-stable solutions of carbonated magnesium ethylate in ethanol for the preservation of paper and for the preparation of catalysts for the polymerization of olefins.

Suitable solutions in accordance with the present invention, are prepared from carbonated magnesium ethylate, using either metallic magnesium (equation 1) or magnesium ethylate (equation 2) as the magnesium source. The use of metallic magnesium is economically more advantageous since magnesium ethylate is usually obtained from magnesium metal by reaction with ethanol, and a reaction step is therefore dispensed with. Furthermore, products of higher color quality can be produced in the reaction of metallic magnesium with ethanol and $CO_2$ according to equation (1). Thus, in the reaction of metallic magnesium with ethanol and $CO_2$, solutions according to the invention are obtained which have slightly lower color numbers, measured according to the Gardner method of measurement, compared with the solutions according to the invention which are prepared from magnesium ethylate and $CO_2$ according to equation (2).

Owing to the fact that, in the reaction of metallic magnesium with ethanol and $CO_2$, the surface of the magnesium is continuously exposed due to the solubility of the carbonated magnesium ethylate, there is no passivation of the metal surface as a result of the formation of an insoluble boundary layer between metal and ethanol. In the preparation of the solutions according to the invention in accordance with equation (1), it is therefore not necessary to rely on the use of surface-rich magnesium material, such as, for example, magnesium turnings or magnesium granules, as is required, for example, in the industrial production of magnesium ethylate, and instead magnesium block material which is cheaper and easier to handle in terms of safety can be used. Furthermore, no auxiliaries, such as, for example, mercury salts (cf. Liebigs Annalen der Chemie (1925) 444: 236), are required for initiating the reaction, so that the achievable product purity when a magnesium metal is used in accordance with equation (1) is slightly greater compared with that when magnesium ethylate is used in accordance with equation (2).

The carbonation can be effected by passing gaseous $CO_2$ into or by adding liquid or solid $CO_2$ to the reaction mixture of ethanol and magnesium according to equation (1) or of ethanol and magnesium ethylate according to equation (2).

The $CO_2$ content (n) of the solution according to the invention can thus be adjusted by metering gaseous, liquid or solid $CO_2$ into the mixture.

In another variant, the $CO_2$ content (n) of the solution according to the invention can be adjusted by thermal expulsion of $CO_2$ from a solution containing an excess of $CO_2$.

The amount of $CO_2$ introduced can be easily monitored via the mass balance, through the weight increase. Owing to the sensitivity of the solutions according to the invention to hydrolysis and to oxidation, all operations must be carried out in the absence of air and moisture.

Solutions of carbonated magnesium ethylate in ethanol having a high $CO_2$ content (n) and at the same time a high magnesium concentration tend to precipitate and form gels. Solutions with low $CO_2$ content (n) tend to strongly discolor with storage within a few weeks.

Solutions of carbonated magnesium ethylate in ethanol having a magnesium content of 4% by weight and having a $CO_2$ content (n) of <1.55 have color numbers of less than 1 (measured according to "Gardner") in the freshly prepared state when magnesium metal is used as a starting material in the synthesis. After storage for 6 weeks, the color deepens continuously to an intense orange.

Solutions of carbonated magnesium ethylate in ethanol having a magnesium content of 4% by weight and having a $CO_2$ content (n) of $\leq 1.55$ have a stable color. Even after storage for several months in tightly sealed glass bottles, no coloration occurs. The "Gardner" color number determined has values of <1. On the other hand, products having a $CO_2$ content (n) of <1.55 which have been stored for about 6 weeks have "Gardner", color numbers of up to 6.

In the case of solutions of carbonated magnesium ethylate in ethanol having a magnesium content of 2.5 to 6% by weight and a $CO_2$ content (n) of >1.85, precipitation occurs after only a few days. Solutions of carbonated magnesium ethylate in ethanol having a magnesium content of 2.5 to 6% by weight and having $CO_2$ contents (n) of <1.85 are, on the other hand, storage-stable for months with regard to precipitation.

Thus, if the $CO_2$ content is limited to values (n) of 1.55 to 1.85 for solutions of carbonated magnesium ethylate in ethanol, magnesium contents of 2.5 to 6% by weight can be established without significant color changes or precipitation occurring during storage of the solutions according to the invention. In the case of lower magnesium contents of the solutions according to the invention, the range of the $CO_2$ content (n) is greater: at a magnesium content of 1.5 to 2.5% by weight, storage stable solutions are obtained for values of the $CO_2$ content (n) in the range from 1.55 to 1.90. In the case of magnesium contents of less than 1.5% by weight, $CO_2$ contents (n) of 1.55 to 2.2 are possible without colorations, precipitation and gel formation occurring during the storage of the solutions according to the invention over long periods.

Solutions or carbonated magnesium ethylate in ethanol having a magnesium content of 4% by weight and a $CO_2$ content (n) of 1.55 to 1.85, prepared by carbonation of commercially available magnesium ethylate (standard particle size, manufacturer Hüls AG) in ethanol, have a color number of 2 to 3 (measured according to "Gardner") shortly after their preparation. If, instead of magnesium ethylate, magnesium block material is used as starting material for the preparation, color numbers of less than 1 (measured according to "Gardner") are obtained in the case of solutions having the same magnesium and $CO_2$ concentrations.

Thus, if metallic magnesium is used as the magnesium source in the preparation of the solutions according to the invention, slightly better products are obtained in terms of purity and color quality than when magnesium ethylate is used as a starting material.

Having generally described this invention, a further understanding can be obtained by reference to certain specific examples which are provided herein for purposes of illustration only and are not intended to be limiting unless otherwise specified.

EXAMPLES

Example 1: Preparation of a storage-stable solution of carbonated magnesium ethylate from magnesium ethylate and $CO_2$ in ethanol 630 g of ethanol were placed in a 2 l three-necked flask equipped with a reflux condenser, a gas inlet tube, a nitrogen blanketing system and a KPG blade stirrer, and 100 g of magnesium ethylate (manufacturer: Hüls AG) were then added while blanketing with nitrogen. $CO_2$ was passed in while stirring. The $CO_2$ absorption was monitored continuously by checking the weight. The temperature in the reaction space was increased continuously. The reaction was terminated on absorption of 66 g of $CO_2$, corresponding to a $CO_2$ content (n) of 1.72. The temperature reached a maximum value of 56° C. The solution thus produced was slightly pink and cloudy. The precipitate settled out completely within three days. The solution was separated from the precipitate by decanting or centrifuging. The resulting solution having a magnesium content of 2.6% by weight was clear and had a color number of 2 (measured according to "Gardner"). Neither discoloration nor precipitation nor gel formation occurred after storage for 6 weeks in a tightly sealed glass bottle.

Example 2: Preparation of a storage-stable solution of carbonated magnesium ethylate from metallic magnesium and $CO_2$ in ethanol 2,374 g of ethanol were placed in a 4 l double-jacketed three-necked flask equipped with a reflux condenser, a gas inlet tube, a nitrogen blanketing system and a KPG blade stirrer, and 121 g of magnesium block material (manufacturer: Normag) which has been sawn to an edge length of 9 cm×2 cm×2 cm were then suspended, while blanketing with nitrogen, in the reaction apparatus by means of stainless steel wire so that it was completely immersed in ethanol. $CO_2$ was passed in while stirring. The $CO_2$ absorption is monitored continuously by checking the weight. A gentle reflux was established by means of thermostating. After the absorption of 378 g of $CO_2$, corresponding to a $CO_2$ content (n) of 1.7, the magnesium had dissolved with evolution of hydrogen, and the reaction was terminated after about 30 hours. The remaining solution was slightly pink and cloudy. The precipitate settled out completely within three days. The solution was separated from the precipitate by decanting or centrifuging. The resulting solution having a magnesium content of 4.2% by weight was clear and had a color number of less than 1 (measured according to "Gardner").

Neither coloration nor precipitation nor gel formation occurred after storage for 6 weeks in a tightly sealed glass bottle.

Comparative Example 1: Preparation of a solution of carbonated magnesium ethylate from magnesium ethylate and $CO_2$ in ethanol, which solution is unstable with regard to color A solution of carbonated magnesium ethylate in ethanol was first prepared analogously to Example 1. In addition, by establishing a gentle reflux, a part of the $CO_2$ was expelled in about 3 hours by boiling. The $CO_2$ content (n) of the solution was 1.13 and the magnesium content was 2.7% by weight. After a storage time of 6 weeks, the solution was orange and the color number increased to a value of 5 (measured according to "Gardner").

Comparative Example 2: Preparation of a solution of carbonated magnesium ethylate from magnesium ethylate and $CO_2$ in ethanol, which solution is unstable with regard to precipitation A solution was first prepared analogously to Example 1. Before separation from the precipitate, the introduction of $CO_2$ was continued. After the additional absorption of 10 g of $CO_2$, corresponding to a present $CO_2$ content (n) of 2.0, the $CO_2$ introduction was terminated and the solution is separated from the precipitate as described in Example 1.

The solution thus obtained and having a magnesium content of 2.6% by weight was completely clear. After a storage time of 6 weeks at room temperature, a crystalline precipitate formed in the solution. The formation of the precipitate was accelerated by storage at temperatures below room temperature. At 10° C., a considerable amount of crystalline precipitate separated out after storage for only a few days.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A storage-stable solution of carbonated magnesium ethylate of the formula $Mg(C_2H_5O)_2 (CO_2)_n$ in ethanol, wherein:

(1) the magnesium content of the solution is of from 2.5 to 6% by weight, based on the total solution, and the $CO_2$ content (n) is of from 1.55 to 1.85;

(2) the magnesium content of the solution is of from 1.5 to 2.5% by weight, based on the total solution, and the $CO_2$ content (n) is of from 1.55 to 1.90; or (3) the magnesium content of the solution is less than 1.5% by weight, based on the total solution, and the $CO_2$ content (n) is of from 1.55 to 2.2.

2. A process for preserving paper comprising coating paper with a solution of carbonated magnesium ethylate in ethanol with $CO_2$, wherein (1) the magnesium content of the solution is of from 2.5 to 6% by weight, based on the total solution, and the $CO_2$ content (n) is of from 1.55 to 1.85;

(2) the magnesium content of the solution is of from 1.5 to 2.5% by weight, based on the total solution, and the $CO_2$ content (n) is of from 1.55 to 1.90; or (3) the magnesium content of the solution is less than 1.5% by weight, based on the total solution, and the $CO_2$ content (n) is of from 1.55 to 2.2.

* * * * *